United States Patent [19]

Beck

[11] Patent Number: 4,631,343
[45] Date of Patent: Dec. 23, 1986

[54] CYANOPYRAZOLE INTERMEDIATES

[75] Inventor: James R. Beck, Indianapolis, Ind.

[73] Assignee: Eli Lilly and Company, Indianapolis, Ind.

[21] Appl. No.: 650,160

[22] Filed: Sep. 13, 1984

Related U.S. Application Data

[63] Continuation-in-part of Ser. No. 549,111, Nov. 7, 1983, abandoned.

[51] Int. Cl.$^4$ .................. C07D 401/04; C07D 231/14
[52] U.S. Cl. .................................... 546/279; 546/162; 548/378
[58] Field of Search ................. 548/378; 546/162, 279

[56]  References Cited

U.S. PATENT DOCUMENTS

| | | | |
|---|---|---|---|
| 4,276,294 | 6/1981 | Bowman | 514/252 |
| 4,353,910 | 10/1982 | Perregaard | 514/302 |
| 4,362,666 | 12/1982 | Wasley | 260/245.7 |
| 4,406,889 | 9/1983 | Hartmann et al. | 514/8 |
| 4,430,344 | 2/1984 | Iwao et al. | 514/365 |

FOREIGN PATENT DOCUMENTS

| | | | |
|---|---|---|---|
| 465117 | 12/1977 | Spain | 548/378 |
| 493459 | 7/1980 | Spain | 548/378 |
| 493457 | 7/1980 | Spain | 548/378 |
| 493458 | 7/1980 | Spain | 548/378 |

OTHER PUBLICATIONS

Battesti et al., Bull. Soc. Chim. France, 1975, No. 5–6, pp. 1268–1270.
Chem Abst., 90, 152223w (1979).
Chem Abst., 96, 142876w (1982).
Translation of *Bull. Soc. Chim. Fr.* 4, 1336–43 (1971).
CA 96, 1982: 142848p.
CA 96, 1982: 142849q.

Primary Examiner—Richard A. Schwartz
Assistant Examiner—Kurt G. Briscoe
Attorney, Agent, or Firm—Kathleen R. S. Page; Joseph A. Jones

[57]  ABSTRACT

5-Cyano-1-substituted-1H-pyrazole-4-carboxylic acids and esters useful as intermediates to the corresponding 4-carboxyamide derivatives having herbicidal and algicidal activity.

15 Claims, No Drawings 4,631,343

CYANOPYRAZOLE INTERMEDIATES

CROSS-REFERENCE TO RELATED APPLICATION

This is a continuation-in-part of my copending application Ser. No. 549,111, filed Nov. 7, 1983 now abandoned.

SUMMARY OF THE INVENTION

The present invention relates to a compound of the formula

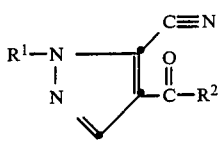

wherein
$R^1$ is $C_1$-$C_6$ alkyl, $C_5$-$C_6$ cycloalkyl,

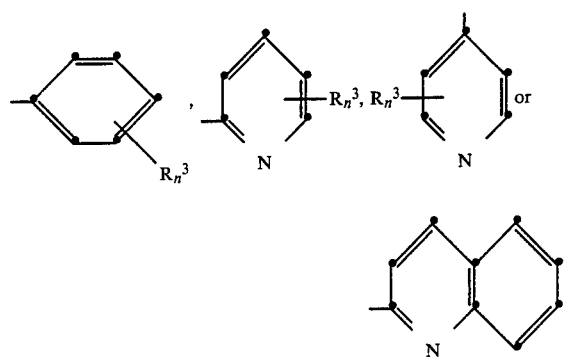

$R^2$ is halogen, hydroxy or $C_1$-$C_6$ alkoxy;
each $R^3$ is independently halogen, $C_1$-$C_4$ alkyl, $C_1$-$C_4$ alkoxy, $C_1$-$C_4$ haloalkyl, $C_1$-$C_4$ haloalkoxy or cyano; and
n is 0-3;
with the proviso that when $R^3$ is $C_1$-$C_4$ alkyl, that substituent exists at other than the 2 or 6 position of the phenyl ring.

These compounds are useful as intermediates to the corresponding 5-cyano-1-substituted-1H-pyrazole-4-carboxamide derivatives having herbicidal and algicidal activity.

DETAILED DESCRIPTION OF THE INVENTION

In the above formula, $C_1$-$C_4$ alkyl represents a straight or branched alkyl chain having form one to four carbon atoms. Typical $C_1$-$C_4$ alkyl groups include methyl, ethyl, n-propyl, isopropyl, n-butyl, sec.-butyl, t-butyl, and the like. The term $C_1$-$C_6$ alkyl includes the foregoing groups as well as $C_5$ and $C_6$ groups such as n-pentyl, tert-pentyl, 3-pentyl, n-hexyl, and 1-methyl-1-ethylpropyl.

$C_1$-$C_6$ Alkoxy represents a straight or branched alkoxy chain having from one to six carbon atoms. Typical $C_1$-$C_6$ alkoxy groups include methoxy, ethoxy, n-propoxy, isopropoxy, n-butoxy, sec.-butoxy, isobutoxy, t-butoxy, n-pentoxy and the like.

The terms "halogen" or "halo" represent fluorine, chlorine, bromine and iodine.

$C_1$-$C_4$ Haloalkyl represents a $C_1$-$C_4$ alkyl group bearing one or more halogen substituents. Such haloalkyl groups include trifluoromethyl, 2,2,2-trifluoroethyl, pentabromoethyl, 3-chloropropyl, 2-iodopropyl, 4-fluorobutyl and the like.

$C_1$-$C_4$ Haloalkoxy is a $C_1$-$C_4$ alkoxy group bearing one or more halogen atoms. Typical members of this classification include trifluoromethoxy, 1,1,2,2-tetrafluoroethoxy, pentafluoroethoxy, 3-bromopropoxy, 4-chlorobutoxy, 4-iodobutoxy and the like.

The 1-aryl or 1-heteroaryl carboxamide derivatives are preferably prepared by the following synthetic process. The process involves reacting a 1-aryl or 1-heteroarylhydrazine derivative with an alkyl(alkoxymethylene)cyanoacetate analog to prepare the corresponding 5-amino-1-substituted-1H-pyrazole-4-carboxylic acid ester. Next, the amino derivative is converted to the halogen derivative to provide the corresponding 5-halopyrazolecarboxylic acid ester derivative. This compound is then converted into the 5-cyanopyrazole carboxylic acid ester, which is finally reacted with an appropriately substituted amine to give the corresponding compound having herbicidal and algicidal activity. The scheme for this reaction is represented by the following:

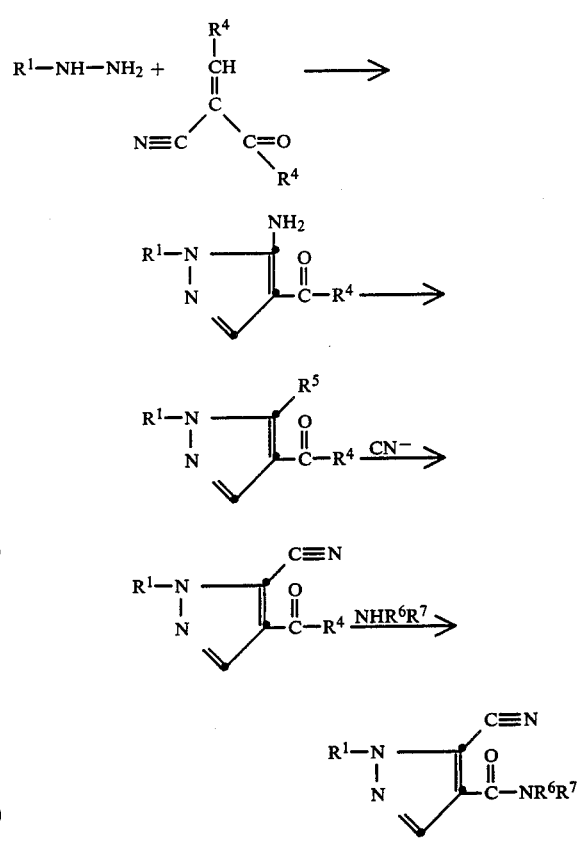

wherein $R^1$ is as defined above, each $R^4$ is independently $C_1$-$C_6$ alkoxy, $R^5$ is halogen and each $R^6$ and $R^7$ independently are hydrogen, $C_1$-$C_4$ alkyl, $C_3$-$C_4$ alkenyl, $C_3$-$C_4$ alkynyl, $C_3$-$C_4$ cycloalkyl or $C_1$-$C_3$ alkoxy with the proviso that when $R^6$ is alkoxy R is other than alkoxy, or when $R^6$ and $R^7$ are taken together with the nitrogen atom to which they are attached, form piperidine, morpholine or pyrrolidine.

The reaction of a 1-aryl or 1-heteroarylhydrazine with an alkyl(alkoxymethylene)cyanoacetate to prepare a 5-amino-4-pyrazolecarboxylic acid ester is readily practiced by well known procedures. Typically equimolar quantities of the two starting materials are combined in a suitable solvent, such as methanol or ethanol. The mixture is stirred at a temperature in the range of from about 20° C. to 200° C., more preferably at reflux temperature of the reaction mixture. The product thus formed after about 2 to 24 hours may then be isolated and purified according to standard procedures.

The 5-halogen-4-pyrazolecarboxylic acid esters used as starting materials in the present reaction scheme are prepared by different procedures depending on the desired halogen atom. Compounds wherein $R^5$ in the above reaction scheme is chlorine are prepared by employing nitrosyl chloride as both the diazotizing and halogenating agent. This reaction is typically performed in a non-reactive organic solvent and preferably in the presence of an acid catalyst. Typical solvents include most halogenated solvents with chloroform and carbon tetrachloride being preferred. An excess of the nitrosyl chloride is typically bubbled into the reaction mixture for about 5 to 30 minutes. The mixture can then be heated on a steam bath for a short period of time. The product may then be isolated by simply removing the volatiles under reduced pressure and purifying the product by common techniques if desired.

Intermediates wherein $R^5$ is bromine or iodine are prepared by employing an alkyl nitrite diazotizing agent and the corresponding halogen source as desired. Typical halogen sources include bromine, iodine, bromoform, iodoform and the like. Suitable alkyl nitrite reagents include, but are not limited to, t-butyl nitrite, isoamyl nitrite and the like. Typically the reaction is performed in a suitable organic solvent such as chloroform or carbon tetrachloride by the addition of the alkyl nitrite dropwise to the reaction mixture. The reaction is usually complete after about 1 to 48 hours when conducted at a temperature between 0° C. and 100° C., more preferably from 10° C. to 50° C. Typically the reaction is worked up by simply evaporating the reaction mixture to dryness under reduced pressure and purifying the residue if desired by standard techniques such as crystallization or column chromatography.

Intermediates wherein $R^5$ is fluorine are prepared by displacing chlorine from the corresponding pyrazolecarboxylic acid ester. This reaction is conducted by adding an excess of fluorinating agent to the appropriate starting material dissolved in a suitable solvent. Suitable solvents include DMF and DMSO with the latter being preferred. Typical fluorinating agents include the alkali metal fluorides such as sodium fluoride, potassium floride and cesium floride. Before being used in the reaction, the fluorinating agent should be dried so as to remove any residual water. Generally this can be performed by refluxing the fluorinating agent in a water immiscible solvent such as toluene. The solvent is then removed before combining the reaction ingredients. The reaction is substantially complete after about 1 to 48 hours when conducted at a temperature in the range from about 75° C. to about 200° C., more preferably from 100° C. to about 150° C. The product is then generally isolated by pouring the cooled reaction mixture into ice water and collecting the precipitated solid by filtration. The product thus isolated may then be purified if desired by routine procedures.

Preparation of the 5-cyano-4-pyrazolecarboxylic acid ester compounds of the invention can also be performed by procedures well known to those skilled in the art. Preferably these compounds are prepared by reacting the 5-halopyrazole derivative with an alkali metal cyanide agent in the presence of a suitable solvent. Suitable solvents include most of the aprotic solvents with DMF, DMSO and hexamethylphosphoramide being preferred. Typical alkali metal cyanide reagents include sodium cyanide, lithium cyanide, potassium cyanide and the like. Typically, these cyanide reagents are dried according to standard procedures to remove any residual moisture. The reaction is substantially complete after about 1 to 48 hours when conducted at a temperature in the range of from about 50° C. to about 200° C. more preferably from about 80° C. to 140° C. The product is then generally isolated by pouring the cooled reaction mixture into ice water and collecting the precipitated solid by filtration. The product thus isolated may then be purified if desired by routine procedures.

The biologically active carboxamides are finally prepared by reacting the 5-cyano-4-pyrazolecarboxylic acid ester compounds of the invention with an appropriately substituted amine under standard reaction conditions. This reaction can be carried out by combining the carboxylic acid derivative with about an equimolar quantity of the amine in mutual solvent such as tetrahydrofuran, diethyl ether, dichloromethane, dioxane, dimethylsulfoxide, dimethylformamide, benzene, toluene and the like. The reaction is substantially complete after about 2 to 200 hours when carried out at a temperature from about 0° C. to 200° C. preferably from about 30° to about 100° C. The product of the reaction may then be isolated by simply removing the reaction solvent, for instance by evaporation under reduced pressure. Also the reaction mixture may be added to water and the product collected by filtration or extracted into a water immiscible solvent. The product thus isolated can be further purified if desired by any one of several well known techniques.

The biologically active carboxamide may also be prepared by hydrolyzing the present 5-cyano-4-pyrazolecarboxylic acid ester compounds as prepared above to the corresponding 5-cyano-4-pyrazolecarboxylic acid compounds of the invention. The carboxamide derivatives are then prepared by the direct coupling of a 5-cyano-4-pyrazolecarboxylic acid with an appropriately substituted amine in the presence of a coupling reagent to provide the corresponding carboxamide according to the following reaction scheme:

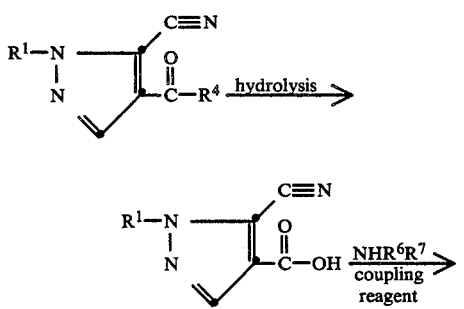

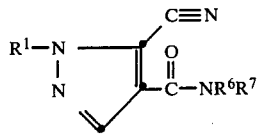

wherein $R^1$, $R^4$, $R^6$ and $R^7$ are as defined above.

This reaction process requires the use of a coupling reagent, for example any of the type of coupling reagents commonly employed in the synthesis of peptides. Examples of such coupling reagents include carbodiimides, such as N,N'-dicyclohexylcarbodiimide, N,N'-diisopropylcarbodiimide of N,N'-diethylcarbodiimide; the imidazoles such as carbonyldiimidazole as well as reagents such as N-ethoxycarbonyl-2-ethoxy-1,2-dihydroquinoline (EEDQ). The direct coupling of a 5-cyano-4-pyrazolecarboxylic acid and an amine is carried out by adding about an equimolar quantity of the amine starting material to a solution of the carboxylic acid in the presence of an equimolar quantity or slight excess of coupling reagent. The reaction generally is carried out in an unreactive organic solvent such as dichloromethane or dimethylformamide and is usually complete within about 24 hours when conducted at a temperature in the range of about 0° C. to about 30° C. The product is then typically isolated by filtration. The carboxamide product thus formed can be further purified if needed by any of several routine methods including crystallization from common solvents, chromatography over solid supports such as silica or alumina, and related purification techniques.

The conversion of the carboxylic acid ester derivative to the present carboxylic acid is accomplished by well known hydrolysis conditions. This reaction is typically performed with a suitable base in a mutual organic solvent such as aqueous methanol or ethanol. Suitable bases include the alkali metal hydroxides, preferably sodium hyroxide and potassium hydroxide. Typically the reaction mixture is refluxed for about 1 to 10 minutes and then acidified. The resulting precipitate may then be either extracted into a water immiscible solvent or collected by filtration. Purification may be performed if desired by any one of several standard techniques.

The carboxamide derivatives may also be prepared by reacting a 5-cyano-4-pyrazolecarboxylic acid halide of the invention with an appropriate amine as defined above according to the general procedure employed with a carboxylic acid ester starting material. A base may also be utilized in the reaction to act as an acid scavenger. The compounds of the invention wherein $R^2$ is halogen are prepared by reacting a 4-pyrazolecarboxylic acid with a known halogenating agent in a suitable solvent typically at an elevated temperature. Exemplary halogenating agents capable for use in this reaction include thionyl chloride, oxalyl chloride, oxalyl bromide and the like. Suitable solvents include most hydrocarbon solvents, preferably benzene, toluene, the xylenes, chloroform, carbon tetrachloride, dichloromethane and the like. The reaction is usually complete after about 30 minutes to 48 hours when conducted at a temperature in the range of from about 40° C. to about 150° C., more preferably at the reflux temperature of the reaction mixture. The reaction is typically worked up by removing the solvent in vacuo and purifying according to normal procedures.

Compounds of the present invention wherein $R^1$ is $C_1$–$C_6$ alkyl or $C_5$–$C_6$ cycloalkyl are prepared according to the following reaction scheme wherein $R^1$ represents $C_1$–$C_6$ alkyl or $C_5$–$C_6$ cycloalkyl and $R^5$, as above, represents $C_1$–$C_6$ alkoxy.

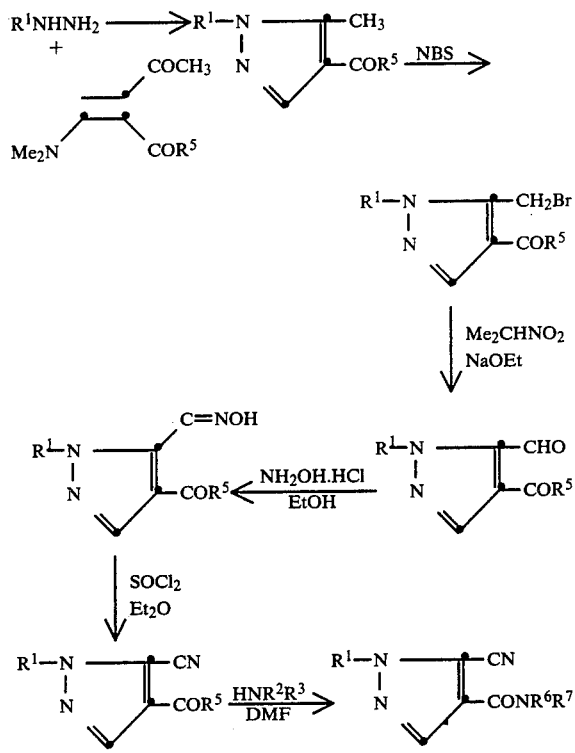

Thus, an alkyl- or cycloalkylhydrazine is reacted with an alkyl α-acetyl-α-(dimethylaminoethylene)acetate to produce a 5-methylpyrazole. The reaction is conducted in a suitable solvent, such as an alkanol, and at temperatures of from 20° C. to 200° C., conveniently at the reflux temperature of the solvent. The product of the reaction is a 5-methyl-1-alkyl or cycloalkyl-1-H-pyrazole-4-carboxylic acid ester.

This product is then brominated to obtain a 5-(bromomethyl) group. Conveniently, N-bromosuccinimide is employed, in a suitable solvent such as carbontetrachloride and at reaction temperatures of from 20° C. to 100° C. The 5-(bromomethyl) product can then be treated in accordance with the procedures of H. B. Hass and M. L. Bender, J. Amer. Chem. Soc., 71, 1967 (1949) to obtain the corresponding 5-formyl compound.

The 5-formyl compound is then reacted with hydroxylamine. The reaction is conducted in a suitable solvent, which can be ethanol or methanol. Suitable reaction temperatures are from 20° C. to 100° C. The reaction yields the 5-(hydroxyiminomethyl) compound, which can be dehydrated to the corresponding 5-cyano compound. The dehydration can be accomplished in any of numerous known methods. One such method is dehydration by the use of thionyl chloride, conducted in a suitable solvent such as ther, toluene, or hexane. Reaction temperatures are desirably 20° C. to 100° C.

As a result of the foregoing reaction, 5-cyano-1-alkyl or cycloalkyl-1H-pyrazole-4-carboxylic esters are produced. They can be converted to the final cyanopyrazole herbicides in accordance with the present invention by the same techniques described above for 1-aryl and 1-heteroaryl compounds of the present invention.

The following Examples are illustrative of compounds of the present invention, as well as methods of their preparation. These examples are not intended to be limiting in any respect and should not be so construed.

EXAMPLE 1

5-Cyano-1-(2-pyridinyl)-1H-pyrazole-4-carboxylic acid, ethyl ester

A. 5-Amino-1-(2-pyridinyl)-1H-pyrazole-4-carboxylic acid, ethyl ester

A solution of 21.83 g of 2-hydrazinopyridine and 38.2 g of ethyl (ethoxymethylene)cyanoacetate dissolved in 150 ml of acetic acid and 50 ml of water was heated on a steam bath for approximately 16 hours. The reaction mixture was allowed to cool to room temperature and placed in a refrigerator whereupon crystals slowly formed. The precipitated solid was collected by filtration and washed with cold 50% aqueous ethanol to provide 23.6 g of 5-amino-1-(2-pyridinyl)-1H-pyrazole-4-carboxylic acid, ethyl ester. Yield 50.9%. mp=89°–91° C.

B. 5-Chloro-1-(2-pyridinyl)-1H-pyrazole-4-carboxylic acid, ethyl ester

Nitrosyl chloride was bubbled through a solution of 23.62 g of 5-amino-1-(2-pyridinyl)-1H-pyrazole-4-carboxylic acid, ethyl ester in 100 ml of chloroform for approximately 5 minutes. The reaction mixture was heated on a steam bath for another 5 minutes and the volatiles were removed under reduced pressure to provide an oil. The residue was cooled in the refrigerator whereupon crystals formed. The solid was crystallized from ethanol and collected by filtration to provide 16.3 g of 5-chloro-1-(2-pyridinyl)-1H-pyrazole-4-carboxylic acid, ethyl ester. Yield 64.8%. mp=50°–51° C.

Analysis calculated for $C_{11}H_{10}ClN_3O_2$: Theory: C, 52.50; H, 4.01; N, 16.70; Found: C, 52.22; H, 3.75; N, 16.59.

C.

A solution of 7.36 g of 5-chloro-1-(2-pyridinyl)-1H-pyrazole-4-carboxylic acid, ethyl ester, 3.2 g of sodium cyanide and 25 ml of DMF was heated at approximately 100° C. for 3 hours. The reaction mixture was cooled and poured into 300 ml of ice water. The precipitated solid was collected by filtration to afford 5.79 of solid. This material was recrystallized from ethanol to provide 4.72 g of 5-cyano-1-(2-pyridinyl)-1H-pyrazole-4-carboxylic acid, ethyl ester. mp=112°–114° C.

Analysis calculated for $C_{12}H_{10}N_4O_2$: Theory: C, 59.50; H, 4.16; N, 23.13; Found: C, 59.43; H, 4.11; N, 23.06.

D.

To a solution of 2.5 g of 5cyano-1-(2-pyridinyl)-1H-pyrazole-4-carboxylic acid, ethyl ester in 20 ml of DMF was added an excess of 40% aqueous monomethylamine so as not to precipitate out the pyrazole starting material. Approximately 24 hours later additional monomethylamine was added to the reaction mixture as well as additional DMF so as to keep these reactants in solution. The reaction mixture was heated and subsequently added to 150 ml of ice water. The precipitated solid was collected by filtration and recrystallized from methanol to afford 1.2 g of 5-cyano-1-(2-pyridinyl)-N-methyl-1H-pyrazole-4-carboxamide. mp=200°–202° C.

Analysis calculated for $C_{11}H_9N_4O$: Theory: C, 58.15; H, 3.99; N, 30.82; Found: C, 57.87; H, 3,83; N, 30.53.

EXAMPLE 2

5-Cyano-1-[2-(trifluoromethyl)-4-chlorophenyl]-1H-pyrazole-4-carboxylic acid, ethyl ester

A.
5-Amino-1-[2-(trifluoromethyl)-4-chlorophenyl]-1H-pyrazole-4-carboxylic acid, ethyl ester A solution of 31.58 g of 2-(trifluoromethyl)-4-chlorophenylhydrazine and 27.92 g of ethyl (ethoxymethylene)cyanoacetate dissolved in 225 ml of acetic acid and 75 ml of water was heated on a steam bath for approximately 16 hours. The reaction mixture was cooled to room temperature and placed in the refrigerator. The precipitated solid was collected by filtrate to provide 43 g of 5-amino-1-[2-(trifluoromethyl)-4-chlorophenyl]-1H-pyrazole-4-carboxylic acid, ethyl ester. mp=114°–116° C.

B.
5-Chloro-1-[2-(trifluoromethyl)-4-chlorophenyl]-1H-pyrazole-4-carboxylic acid, ethyl ester Hydrochloric acid gas was bubbled through a solution of 26 g of 5-amino-1-[2-(trifluoromethyl)-4-chlorophenyl]-1H-pyrazole-4-carboxylic acid, ethyl ester dissolved in 250 ml of chloroform for 1 minute. Nitrosyl chloride was next bubbled through the solution for 10 minutes. The reaction mixture was then heated on a steam bath and the volatiles were removed under reduced pressure. The residue was dissolved in hot ethanol, purified with charcoal and the product crystallized to provide 16.6 g of 5-chloro-1-[2-(trifluoromethyl)-4-chlorophenyl]-1H-pyrazole-4-carboxylic acid, ethyl ester. mp=67°–69° C.

Analysis calculated for $C_{13}H_9Cl_2F_3N_2O_2$: Theory: C, 44.22; H, 2.57; N, 7.93; Found: C, 44.48; H, 2.33; N, 7.80.

C.

A solution of 3.15 g of 5-chloro-1-[2-(trifluoromethyl)-4-chlorophenyl]-1H-pyrazole-4-carboxylic acid, ethyl ester and 1.1 g of sodium cyanide in 25 ml of dimethylformamide was heated at approximately 100° C. for four and one-half hours. The reaction mixture also contained approximately 3 g of molecular sieve to insure dryness. The reaction mixture was cooled and poured into approximately 300 ml of ice water. The precipitated solid was collected by filtration and recrystallized from ethanol (charcoal) to provide 1 g of 5-cyano-1-[2-(trifluoromethyl)-4-chlorophenyl]-1H-pyrazole-4-carboxylic acid, ethyl ester. mp=70°–72° C.

Analysis calculated for $C_{14}H_9ClF_3N_3O_2$: Theory: C, 48.93; H, 2.64; N, 12.23; Found: C, 49.16; H, 2.39; N, 11.93.

D.

A solution of 1.23 g of 5-cyano-1-[2-(trifluoromethyl)-4-chlorophenyl]-1H-pyrazole-4-carboxylic acid, ethyl ester and 8 ml of 40% aqueous monomethylamine in 20 ml of DMF was stirred at approximately 25° C. for 16 hours. The reaction mixture was poured into 150 ml of ice water and the precipitated solid was collected by filtration. The isolated material was recrystallized from ethanol to provide 535 mg of 5-cyano-1-[2-(trifluoromethyl)-4-chlorophenyl]-N-methyl-1H-pyrazole-4-carboxamide. mp=162.5°-164° C.

Analysis calculated for $C_{13}H_8ClF_3N_4O$: Theory: C, 47.51; H, 2.45; N, 17.05; Found: C, 47.74; H, 2.67; N, 17.20.

EXAMPLE 3

5-Cyano-1-(2,4-dichlorophenyl)-1H-pyrazole-4-carboxylic acid, ethyl ester

A.

A solution of 6.4 g of 5-chloro-1-(2,4-dichlorophenyl)-1H-pyrazole-4-carboxylic acid, ethyl ester and 2 g of lithium cyanide dissolved in 30 ml of DMF was reacted at approximately 110° C. for 23 hours. One additional gram of lithium cyanide was added to the reaction mixture which was heated for an additional 7 hours. The mixture was poured into ice water and the precipitated solid was collected by filtration and recrystallized from 3A alcohol (charcoal) to provide 3.75 g of 5-cyano-1-(2,4-dichlorophenyl)-1H-pyrazole-4-carboxylic acid, ethyl ester. Yield 61%. mp=79°-81° C.

Analysis calculated for $C_{13}H_9Cl_2N_3O_2$: Theory: C, 50.35; H, 2.93; N, 13.55; Found: C, 50.12; H, 3.11; N, 13.29.

B.

To a solution of 2.5 g of 5-cyano-1-(2,4-dichlorophenyl)-1H-pyrazole-4-carboxylic acid, ethyl ester in 20 ml of DMF was added 20 ml of 40% aqueous monomethylamine. The reaction mixture was stirred at room temperature for approximately two and one-half hours whereupon the solution was poured into ice water. The precipitate was collected by filtration and recrystallized from methanol/water to afford 1.3 g of 5-cyano-1-(2,4-dichlorophenyl)-N-methyl-1H-pyrazole-4-carboxamide. mp=182°-183° C.

Analysis calculated for $C_{12}H_8Cl_2N_4O$: Theory: C, 48.84; H, 2.73; N, 18.98; Found: C, 48.69; H, 2.74; N, 19.23.

EXAMPLE 4

5-Cyano-1-(4-bromophenyl)-1H-pyrazole-4-carboxylic acid, ethyl ester

A solution of 6.6 g of 5-chloro-1-(4-bromophenyl)-1H-pyrazole-4-carboxylic acid, ethyl ester in 30 ml of DMF with 2 g of sodium cyanide was heated at approximately 95° C. for 3 hours. The reaction mixture was poured into ice water and the precipitated solid was collected by filtration. The product was recrystallized from 3A alcohol to afford 5.3 g of 5-cyano-1-(4-bromophenyl)-1H-pyrazole-4-carboxylic acid, ethyl ester. mp=104°-105° C.

Analysis calculated for $C_{13}H_{10}BrN_3O_2$: Theory: C, 48.77; H, 3.15; N, 13.13; Found: C, 48.90; H, 2.91; N, 13.23.

B.

A solution of 3.2 g of 5-cyano-1-(4-bromophenyl)-1H-pyrazole-4-carboxylic acid, ethyl ester in 40 ml of 3A alcohol and 10 ml of 40% aqueous monomethylamine was refluxed for approximately 2 hours. Ten additional milliliters of 40% aqueous monomethylamine was added to the reaction mixture which was then refluxed for an additional 3 hours. The mixture was cooled and the precipitated solid was collected by filtration to provide 1 g of 5-cyano-1-(4-bromophenyl)-N-methyl-1H-pyrazole-4-carboxamide. mp=240°-241° C.

Analysis calculated for $C_{12}H_9BrN_4O$: Theory: C, 47.29; H, 2.97; N, 18.36; Found: C, 47.39; H, 3.07; N, 18.49.

EXAMPLE 5

5-Cyano-1-(4-bromophenyl)-1H-pyrazole-4-carboxylic acid

A.

A hot solution of 8.2 g of potassium hydroxide in 155 ml of 3A ethanol was added to a hot solution of 18.7 g of 5-cyano-1-(4-bromophenyl)-1H-pyrazole-4-carboxylic acid, ethyl ester in 315 ml of 3A ethanol. The salt that precipitated out of solution was dissolved in 2 l. of hot water and acidified with hydrochloric acid. The solid was collected by filtration and dried to afford 16.24 g of 5-cyano-1-(4-bromophenyl)-1H-pyrazole-4-carboxylic acid. mp=209°-211° C.

Analysis calculated for $C_{11}H_6BrN_3O_2$ Theory: C, 45.23; H, 2.07; N, 14.39; Found: C, 45.29; H, 2.10; N, 14.10.

B.

A solution 2.06 g of 5-cyano-1-(4-bromophenyl)-1H-pyrazole-4-carboxylic acid and 1.4 g of carbonyldiimidazole in 25 ml of DMF was stirred at room temperature for approximately 15 minutes. Ten milliliters of 40% aqueous dimethylamine was added to the reaction mixture which was stirred for about four hours at room temperature. The reaction mixture was poured into ice water and the precipitated solid was collected by filtration and dried to provide 1.79 g of product. This material was recrystallized from ethanol to afford 1.42 g of 5-cyano-1-(4-bromophenyl)-N,N-dimethyl-1H-pyrazole-4-carboxamide. mp=131°-133° C.

Analysis calculated for $C_{13}H_{11}BrN_4O$: Theory: C, 48.92; H, 3.47; N, 17.55; Found: C, 48.79; H, 3.52; N, 17.51.

The following compounds were prepared by the general procedures outlined above.

EXAMPLE 6

5-Cyano-1-(4-chlorophenyl)-1H-pyrazole-4-carboxylic acid, ethyl ester mp=84°-85.5° C.

Analysis calculated for $C_{13}H_{10}ClN_3O_2$: Theory: C, 56.64; H, 3.66; N, 15.24; Found: C, 56.49; H, 3.85; N, 15.08.

EXAMPLE 7

5-Cyano-1-(3-bromophenyl)-1H-pyrazole-4-carboxylic acid, ethyl ester mp=93°-94° C.

Analysis calculated for $C_{13}H_{10}BrN_3O_2$: Theory: C, 48.77; H, 3.15; N, 13.13; Found: C, 49.07; H, 3.21; N, 12.98.

EXAMPLE 8

5-Cyano-1-[3-(trifluoromethyl)phenyl]-1H-pyrazole-4-carboxylic acid, ethyl ester mp=59°-60° C.

Analysis calculated for $C_{14}H_{10}F_3N_3O_2$: Theory: C, 54.38; H, 3.26; N, 13.59; Found: C, 54.49; H, 3.16; N, 13.44.

EXAMPLE 9

5-Cyano-1-(2,4-dibromophenyl)-1H-pyrazole-4-carboxylic acid, ethyl ester mp=87°–90° C.

EXAMPLE 10

5-Cyano-1-(3-methylphenyl)-1H-pyrazole-4-carboxylic acid, ethyl ester mp=56°–57.5° C.

Analysis calculated for $C_{14}H_{13}N_3O_2$: Theory: C, 65.87; H, 5.13; N, 16.46; Found: C, 66.13; H, 5.26; N, 16.32.

EXAMPLE 11

5-Cyano-1-(4-pyridinyl)-1H-pyrazole-4-carboxylic acid, ethyl ester mp=91°–93° C.

EXAMPLE 12

5-Cyano-1-(3-chlorophenyl)-1H-pyrazole-4-carboxylic acid, ethyl ester mp=87°–89° C.

Analysis calculated for $C_{13}H_{10}ClN_3O_2$: Theory: C, 56.64; H, 3.66; N, 15.24; Found: C, 56.43; H, 3.39; N, 15.00.

EXAMPLE 13

5-Cyano-1-(5-chloro-2-pyridinyl)-1H-pyrazole-4-carboxylic acid, ethyl ester mp=105°–107° C.

Analysis calculated for $C_{12}H_9ClN_4O_2$: Theory: C, 52.09; H, 3.28; N, 20.25; Found: C, 52.09; H, 3.26; N, 20.34.

EXAMPLE 14

5-Cyano-1-(2-chlorophenyl)-1H-pyrazole-4-carboxylic acid mp=193°–195° C.

Analysis calculated for $C_{11}H_6ClN_3O_2$: Theory: C, 53.35; H, 2.44; N, 16.97; Found: C, 53.05; H, 2.27; N, 16.75.

EXAMPLE 15

5-Cyano-1-(2-chlorophenyl)-1H-pyrazole-4-carboxylic acid, ethyl ester mp=69°–71° C.

Analysis calculated for $C_{13}H_{10}ClN_3O_2$: Theory: C, 56.64; H, 3.66; N, 15.24; Found: C, 56.40; H, 3.71; N, 14.91.

EXAMPLE 16

5-Cyano-1-(4-methoxyphenyl)-1H-pyrazole-4-carboxylic acid, ethyl ester mp=119°–121° C.

Analysis calculated for $C_{14}H_{13}N_3O_3$: Theory: C, 61.99; H, 4.83; N, 15.49; Found: C, 62.27; H, 4.99; N, 15.47.

EXAMPLE 17

5-Cyano-1-(3,4-dichlorophenyl)-1H-pyrazole-4-carboxylic acid, ethyl ester mp=115°–117° C.

Analysis calculated for $C_{13}H_9Cl_2N_3O_2$: Theory: C, 50.35; H, 2.93; N, 13.55; Found: C, 50.10; H, 2.71; N, 13.57.

EXAMPLE 18

5-Cyano-1-[2-(trifluoromethyl)phenyl]-1H-pyrazole-4-carboxylic acid, ethyl ester mp=88°–90° C.

Analysis calculated for $C_{14}H_{10}F_3N_3O_2$: Theory: C, 54.38; H, 3.26; N, 13.59; Found: C, 54.28; H, 3.33; N, 13.41.

EXAMPLE 19

5-Cyano-1-(4-fluorophenyl)-1H-pyrazole-4-carboxylic acid, ethyl ester mp=106°–108° C.

Analysis calculated for $C_{13}H_{10}FN_3O_2$: Theory: C, 60.23; H, 3.89; N, 16.21; Found: C, 60.33; H, 3.99; N, 16.05.

EXAMPLE 20

5-Cyano-1-(3-chloro-4-methylphenyl)-1H-pyrazole-4-carboxylic acid, ethyl ester mp=104°–106° C.

Analysis calculated for $C_{14}H_{12}ClN_3O_2$: Theory: C, 58.04; H, 4.17; N, 14.50; Found: C, 57.88; H, 3.91; N, 14.53.

EXAMPLE 21

5-Cyano-1-(2,3-dichlorophenyl)-1H-pyrazole-4-carboxylic acid, ethyl ester mp=117°–119° C.

Analysis calculated for $C_{13}H_9Cl_2N_3O_2$: Theory: C, 50.35; H, 2.93; N, 13.32; Found: C, 50.08; H, 2.83; N, 13.30.

EXAMPLE 22

5-Cyano-1-(3,4-dimethylphenyl)-1H-pyrazole-4-carboxylic acid, ethyl ester mp=72°–74° C.

Analysis calculated for $C_{15}H_{15}N_3O_2$: Theory: C, 66.90; H, 5.61; N, 15.60; Found: C, 66.78; H, 5.67; N, 15.47.

EXAMPLE 23

5-Cyano-1-(2-quinolinyl)-1H-pyrazole-4-carboxylic acid, ethyl ester mp=155°–157° C.

Analysis calculated for $C_{16}H_{12}N_4O_2$: Theory: C, 65.75; H, 4.14; N, 19.17; Found: C, 65.82; H, 4.32; N, 19.33.

EXAMPLE 24

5-Cyano-1-phenyl-1H-pyrazole-4-carboxylic acid, ethyl ester mp=75°–77° C.

Analysis calculated for $C_{13}H_{11}N_3O_2$: Theory: C, 64.72; H, 4.60; N, 17.42; Found: C, 64.56; H, 4.32; N, 17.36.

EXAMPLE 25

5-Cyano-1-(2,4-dichlorophenyl)-1H-pyrazole-4-carboxylic acid mp=226°–228° C.

Analysis calculated for $C_{11}H_5Cl_2N_3O_2$: Theory: C, 46.84; H, 1.79; N, 14.90; Found: C, 47.06; H, 1.75; N, 14.68.

EXAMPLE 26

5-Cyano-1-(2,5-dichlorophenyl)-1H-pyrazole-4-carboxylic acid, ethyl ester mp=110°-111° C.

Analysis calculated for $C_{13}H_9Cl_2N_3O_2$: Theory: C, 50.32; H, 2.90; N, 13.55; Found: C, 50.22; H, 2.88; N, 13.40.

EXAMPLE 27

5-Cyano-1-(4-methylphenyl)-1H-pyrazole-4-carboxylic acid, ethyl ester mp=77°-78° C.

Analysis calculated for $C_{14}H_{13}N_3O_2$: Theory: C, 65.87; H, 5.13; N, 16.46; Found: C, 65.61; H, 4.99; N, 16.24.

EXAMPLE 28

5-Cyano-1-(3-cyanophenyl)-1H-pyrazole-4-carboxylic acid, ethyl ester mp=118°-120° C.

Analysis calculated for $C_{14}H_{10}N_4O_3$: Theory: C, 63.15; H, 3.79; N, 21.04; Found: C, 62.94; H, 4.02; N, 20.92.

EXAMPLE 29

5-Cyano-1-(3-cyanophenyl)-1H-pyrazole-4-carboxylic acid mp=190°-192° C.

EXAMPLE 30

5-Cyano-1-(4-chlorophenyl)-1H-pyrazole-4-carboxylic acid mp=192°-195° C.

Analysis calculated for $C_{11}H_6ClN_3O_2$: Theory: C, 53.35; H, 2.44; N, 16.97; Found: C, 53.24; H, 2.50; N, 16.73.

EXAMPLE 31

5-Cyano-1-(3-chloro-4-methylphenyl)-1H-pyrazole-4-carboxylic acid mp=207°-209° C.

Analysis calculated for $C_{12}H_8ClN_3O_2$: Theory: C, 55.08; H, 3.08; N, 16.06; Found: C, 55.33; H, 3.26; N, 16.21.

EXAMPLE 32

5-Cyano-1-(3-bromophenyl)-1H-pyrazole-4-carboxylic acid mp=221°-223° C.

Analysis calculated for $C_{11}H_6BrN_3O_2$: Theory: C, 45.23; H, 2.07; N, 14.39; Found: C, 47.47; H, 2.26; N, 14.15.

EXAMPLE 33

5-Cyano-1-[3-(trifluoromethyl)phenyl]-1H-pyrazole-4-carboxylic acid mp=187°-189° C.

Analysis calculated for $C_{12}H_6F_3N_3O_2$: Theory: C, 51.26; H, 2.15; N, 14.94; Found: C, 51.47; H, 2.25; N, 15.02.

EXAMPLE 34

5-Cyano-1-(3-fluorophenyl)-1H-pyrazole-4-carboxylic acid mp=182°-183° C.

Analysis calculated for $C_{11}H_6FN_3O_2$: Theory: C, 57.15; H, 2.62; N, 18.18; Found: C, 56.91; H, 2.84; N, 17.93.

EXAMPLE 35

5-Cyano-1-(3-chlorophenyl)-1H-pyrazole-4-carboxylic acid mp=206°-208° C.

Analysis calculated for $C_{11}H_6ClN_3O_2$: Theory: C, 53.35; H, 2.44; N, 16.97; Found: C, 53.47; H, 2.54; N, 17.01.

EXAMPLE 36

5-Cyano-1-(2-pyridinyl)-1H-pyrazole-4-carboxylic acid mp=224°-226° C.

EXAMPLE 37

5-Cyano-1-(4-methoxyphenyl)-1H-pyrazole-4-carboxylic acid mp=182°-183° C.

Analysis calculated for $C_{12}H_9N_3O_3$: Theory: C, 59.26; H, 3.73; N, 17.28; Found: C, 59.51; H, 3.50; N, 17.08.

EXAMPLE 38

5-Cyano-1-(3,4-dichlorophenyl)-1H-pyrazole-4-carboxylic acid mp=209°-211° C.

Analysis calculated for $C_{11}H_5Cl_2N_3O_2$: Theory: C, 46.84; H, 1.79; N, 14.90; Found: C, 47.03; H, 1.92; N, 14.72.

EXAMPLE 39

5-Cyano-1-(4-fluorophenyl)-1H-pyrazole-4-carboxylic acid mp=179°-181° C.

EXAMPLE 40

5-Cyano-1-(2-quinolinyl)-1H-pyrazole-4-carboxylic acid mp=223°-224° C.

Analysis calculated for $C_{14}H_8N_4O_2$: Theory: C, 63.64; H, 3.05; N, 21.20; Found: C, 63.89; H, 3.10; N, 20.97.

EXAMPLE 41

5-Cyano-1-phenyl-1H-pyrazole-4-carboxylic acid mp=205°-206° C.

Analysis calculated for $C_{11}H_7N_3O_2$: Theory: C, 61.97; H, 3.31; N, 19.71; Found: C, 62.24; H, 3.13; N, 19.65.

EXAMPLE 42

5-Cyano-1-(4-methylphenyl)-1H-pyrazole-4-carboxylic acid mp=200°-201° C.

Analysis calculated for $C_{12}H_9N_3O_2$: Theory: C, 63.43; H, 3.99; N, 18.49; Found: C, 63.20; H, 3.96; N, 18.39.

EXAMPLE 43

5-Cyano-1-(3-fluorophenyl)-1H-pyrazole-4-carboxylic acid, ethyl ester (17% methyl ester)

mp=66°-67° C.

EXAMPLE 44

5-Cyano-1-tert-butyl-1H-pyrazole-4-carboxylic acid, ethyl ester

A. 5-Methyl-1-tert-butyl-1H-pyrazole-4-carboxylic acid, ethyl ester tert-Butylhydrazine hydrochloride (33.6 grams, 0.27 mole) and α-acetyl-α-(dimethylaminomethylene)acetic acid, ethyl ester (50 grams, 0.27 mole) were added to 150 ml. of ethanol and the resulting reaction mixture was refluxed for two hours. The reaction mixture was then cooled, and the solvent was removed in vacuo. The residue was taken up in 300 ml. of ether, washed with water, washed with saturated sodium bicarbonate, washed with saturated brine, and dried using sodium sulfate and filter paper. The solvent was then removed in vacuo. The residue was distilled at 110° C. at 1.2 mm mercury pressure to provide 49.7 grams of 5-methyl-1-tert-butyl-1H-pyrazole-4-carboxylic acid, ethyl ester. Yield 88.0%.

Analysis calculated for $C_{11}H_{18}N_2O_2$: Theory: C, 62.83; H, 8.63; N, 13.32; Found: C, 62.88; H, 8.86; N, 13.50.

B. 5-(Bromomethyl)-1-tert-butyl-1H-pyrazole-4-carboxylic acid, ethyl ester

5-Methyl-1-tert-butyl-1H-pyrazole-4-carboxylic acid, ethyl ester (30 grams, 0.14 mole) and N-bromosuccinimide (25.4 grams, 0.14 mole) were combined in 100 ml. of carbon tetrachloride. A heating lamp was turned onto the reaction mixture, and the reaction mixture was refluxed for three hours. The reaction mixture was then cooled and filtered to remove the succinimide. The filtrate was washed with water, washed with saturated brine, and dried over sodium sulfate and filter paper. The solvent was then removed in vacuo, providing 34.5 grams of the 5-(bromomethyl)-1-tert-butyl-1H-pyrazole-4-carboxylic acid, ethyl ester.

Analysis calculated for $C_{11}H_{17}BrN_2O_2$: Theory: C, 45.69; H, 5.93; N, 9.69; Br, 27.63; Found: C, 45.76; H, 5.65; N, 9.86; Br, 27.56.

C. 5-Formyl-1-tert-butyl-1H-pyrazole-4-carboxylic acid, ethyl ester

This reaction was conducted in accordance with the procedure described by H. B. Hass and M. L. Bender in *J. Am. Chem. Soc.*, 71 1767 (1949). Sodium (1.6 grams, 0.07 mole) was dissolved in 50 ml. of absolute ethanol. Subsequently, 2-nitropropane (8.1 grams, 0.09 mole) and 5-(bromomethyl)-1-tert-butyl-1H-pyrazole-4-carboxylic acid, ethyl ester (20 grams, 0.07 mole) were added. The resulting reaction mixture was refluxed for two hours, then cooled and the solvent removed in vacuo. The residue was taken up in ether, washed with water, washed with 1N sodium hydroxide, washed with saturated brine, and dried using sodium sulfate and filter paper. The solvent was removed in vacuo and the residue was distilled at 110° C. at 1.6 mm mercury pressure, yielding 11 grams of the 5-formyl-1-tert-butyl-1H-pyrazole-4-carboxylic acid, ethyl ester.

Analysis calculated for $C_{11}H_{16}N_2O_3$: Theory: C, 58.91; H, 7.19; N, 12.49; Found: C, 58.78; H, 7.20; N, 12.72.

D. 5-(Hydroxyiminomethyl)-1-tert-butyl-1H-pyrazole-4-carboxylic acid, ethyl ester Hydroxylamine hydrochloride (4.3 grams, 0.062 mole) was added to a cold solution of 5-formyl-1-tert-butyl-1H-pyrazole-4-carboxylic acid, ethyl ester (7 grams, 0.031 mole) in absolute ethanol (40 ml.). The reaction mixture was stirred in the cold for thirty minutes, then at room temperature for 16 hours. The reaction mixture was then poured over ice-water, and the precipitated product was separated, dried, and recrystallized from toluene, yielding 3 grams of 5-(hydroxyiminomethyl)-1-tert-butyl-1H-pyrazole-4-carboxylic acid, ethyl ester, m.p., 105°-107° C.

Analysis calculated for $C_{11}H_{16}N_3O_3$: Theory: C, 55.22; H, 7.16; N, 17.56; Found: C, 55.43; H, 7.21; N, 17.65.

E. 5-Cyano-1-tert-butyl-1H-pyrazole-4-carboxylic acid, ethyl ester

Thionyl chloride (6.6 ml., 0.092 mole) was added to a cold solution of 5-(hydroxyiminomethyl)-1-tert-butyl-1H-pyrazole-4-carboxylic acid, ethyl ester (11 grams, 0.046 mole) in 75 ml. of ether. The solution was stirred in the cold for thirty minutes, then at room temperature for 16 hours. Water was added to the reaction mixture to neutralize the remaining thionyl chloride, then the reaction mixture was poured into a separatory funnel. The phases were separated and the organic phase was washed with water and dried using sodium sulfate and filter paper. The solvent was removed in vacuo, yielding 8.5 grams of 5-cyano-1-tert-butyl-1H-pyrazole-4-carboxylic acid, ethyl ester.

EXAMPLE 45

5-Cyano-1-tert-butyl-1H-pyrazole-4-carboxylic acid

Potassium hydroxide (1.7 grams, 0.027 mole) was dissolved in 20 ml. of ethanol. This solution was poured into a refluxing solution of 5-cyano-1-tert-butyl-1H-pyrazole-4-carboxylic acid, ethyl ester, in 50 ml. of ethanol. The reaction mixture was heated on a steam bath for five minutes, then poured into ice-water, filtered, and acidified with concentrated hydrochloric acid. The precipitated product was collected and dried, yielding 3.2 grams of 5-cyano-1-tert-butyl-1H-pyrazole-4-carboxylic acid (72% yield).

As described above, the compounds of the present invention are useful as intermediates in the synthesis of the corresponding carboxamide derivatives. In turn the carboxamide derivatives have exhibited useful terrestrial and aquatic herbicidal activity, as well as aquatic algicidal activity.

When used as terrestrial herbicides the carboxamide compounds are applied to undesired plants, or to the locus of the plants for which control is desired, in a growth inhibiting amount. This amount will generally be from about 0.05 to about 20.0 pounds or greater of a carboxamide compound per acre (about 0.056 to about 22.4 kg/ha). The compounds are more preferably applied at rates of about 0.10 to about 8.0 pounds per acre (about 0.112 to about 8.96 kg/ha). The exact concentration of active ingredient required varies with the weed species to be controlled, type of formulation. soil type, climate conditions and the like.

When the carboxamide compounds are used as aquatic herbicides, the aquatic plants, for which control of growth is sought are contacted with a carboxamide derivative directly or through the water containing said plants. Generally the compounds are applied at rates in the range of from about 15.0 ppm to about 0.1 ppm, more preferably from about 10.0 ppm to about 0.5 ppm. The optimum concentration of active ingredient necessary to control the growth of aquatic plants varies with the temperature, the species to be controlled, and the type and shape of the body of water to be treated.

When used as aquatic algicides the carboxamide compounds are generally applied at rates effective to inhibit the growth of algae without causing significant toxicity to other aquatic life. The compounds are applied at rates in the range of from about 20.0 ppm to about 0.1 ppm, more preferably at 10.0 ppm to 0.5 ppm.

I claim:

1. A compound of the formula

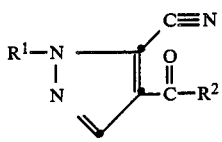

wherein $R^1$ is $C_5$–$C_6$ cycloalkyl,

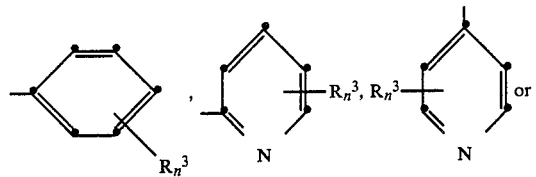

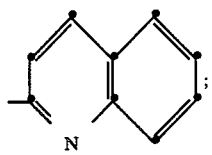

$R^2$ is halogen, hydroxy or $C_1$–$C_6$ alkoxy;

each $R^3$ is independently halogen, $C_1$–$C_4$ alkyl, $C_1$–$C_4$ alkoxy, $C_1$–$C_4$ haloalkyl, $C_1$–$C_4$ haloalkoxy or cyano; and n is 0–3;

with the proviso that when $R_3$ is $C_1$–$C_4$ alkyl, that substituent exists at other than the 2 or 6 position of the phenyl ring.

2. A compound of claim 1 wherein $R^1$ is

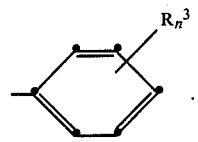

3. A compound of claim 2 wherein $R^2$ is $C_1$–$C_6$ alkoxy.

4. The compound of claim 3 which is 5-cyano-1-(2,4-dichlorophenyl)-1H-pyrazole-4-carboxylic acid, ethyl ester.

5. The compound of claim 3 which is 5-cyano-1-(4-bromophenyl)-1H-pyrazole-4-carboxylic acid, ethyl ester.

6. The compound of claim 3 which is 5-cyano-1-phenyl-1H-pyrazole-4-carboxylic acid, ethyl ester.

7. The compound of claim 3 which is 5-cyano-1-(4-chlorophenyl)-1H-pyrazole-4-carboxylic acid, ethyl ester.

8. A compound of claim 2 wherein $R^2$ is hydroxy.

9. The compound of claim 8 which is 5-cyano-1-(4-bromophenyl)-1H-pyrazole-4-carboxylic acid.

10. The compound of claim 8 which is 5-cyano-1-phenyl-1H-pyrazole-4-carboxylic acid.

11. A compound of claim 1 wherein $R^1$ is

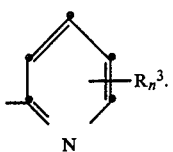

12. A compound of claim 11 wherein $R^2$ is $C_1$–$C_6$ alkoxy.

13. The compound of claim 12 which is 5-cyano-1-(2-pyridinyl)-1H-pyrazole-4-carboxylic acid, ethyl ester.

14. A compound of claim 11 wherein $R^2$ is hydroxy.

15. The compound of claim 14 which is 5-cyano-1-(2-pyridinyl)-1H-pyrazole-4-carboxylic acid.

* * * * *